United States Patent
Cox

(10) Patent No.: US 11,179,265 B2
(45) Date of Patent: *Nov. 23, 2021

(54) SHOULDER AND ARM RESTRAINT

(71) Applicant: XTREME ORTHOPEDICS LLC, Fayetteville, AR (US)

(72) Inventor: Wesley Cox, Fayetteville, AR (US)

(73) Assignee: XTREME ORTHOPEDICS LLC, Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,644

(22) Filed: Aug. 30, 2019

(65) Prior Publication Data

US 2019/0380859 A1 Dec. 19, 2019

Related U.S. Application Data

(63) Continuation of application No. 13/905,337, filed on May 30, 2013, now Pat. No. 10,398,585, and a continuation of application No. 14/444,733, filed on Jul. 28, 2014, now abandoned, which is a continuation of application No. 13/731,289, filed on Dec. 31, 2012, now Pat. No. 8,821,425.

(51) Int. Cl.
*A61F 5/37* (2006.01)

(52) U.S. Cl.
CPC .......... *A61F 5/3738* (2013.01); *A61F 5/3753* (2013.01)

(58) Field of Classification Search
CPC .... A61F 5/3723; A61F 5/3738; A61F 5/3753; A61F 5/373; A61F 5/05858; A61F 5/3746; A45F 3/02; A45F 2200/0516; A45F 2200/0525; A45F 2200/0558; A45F 2200/0575; A45C 9/00

USPC ..................................... 128/869, 878; 604/4
See application file for complete search history.

(56) References Cited

U.S. PATENT DOCUMENTS

| 1,473,041 A | 11/1923 | Ennis |
| 2,211,203 A | 8/1940 | Goldman |
| 2,594,809 A | 4/1952 | Isador |

(Continued)

FOREIGN PATENT DOCUMENTS

| AU | 2007309344 A1 | 6/2009 |
| CA | 2667760 A1 | 5/2008 |

(Continued)

OTHER PUBLICATIONS

"Final Office Action received for U.S. Appl. No. 29/657,371 dated May 21, 2020."

(Continued)

*Primary Examiner* — Camtu T Nguyen
(74) *Attorney, Agent, or Firm* — Kutak Rock LLP

(57) ABSTRACT

A therapeutic orthopedic device is described. The orthopedic device serves to restrain and limit movement of a human arm and shoulder. The device comprises a torso pillow, a padded forearm support attached to the pillow and a shoulder strap that traverses the clavicle region of the opposite shoulder. The pillow is positioned to rest against the torso of a user and the strap is positioned over the opposite shoulder. The forearm support acts as a shelf upon which the user's forearm may rest in a natural position. Flexible straps extend from the forearm support, over the user's forearm, and engage with the pillow to secure the forearm.

8 Claims, 9 Drawing Sheets

(56) References Cited

U.S. PATENT DOCUMENTS

| | | |
|---|---|---|
| 3,074,405 A | 1/1963 | Duensing |
| 3,075,521 A | 1/1963 | Simon |
| 3,508,544 A | 4/1970 | Moore et al. |
| 3,521,623 A | 7/1970 | Nichols et al. |
| 3,678,926 A | 7/1972 | Strittmatter |
| 3,696,810 A | 10/1972 | Gaylord |
| 3,897,777 A | 8/1975 | Morrison |
| 3,934,583 A | 1/1976 | Hollingshead et al. |
| 3,942,525 A | 3/1976 | Dragan |
| 4,066,084 A | 1/1978 | Tillander |
| D248,872 S | 8/1978 | Thomas |
| D251,682 S | 4/1979 | Levine |
| 4,215,687 A | 8/1980 | Shaw |
| 4,243,028 A | 1/1981 | Puyana |
| 4,334,528 A | 6/1982 | Gauvry |
| D265,590 S | 7/1982 | Gauvry |
| 4,370,978 A | 2/1983 | Palumbo |
| 4,378,009 A | 3/1983 | Rowley et al. |
| 4,474,573 A | 10/1984 | Detty |
| 4,598,701 A | 7/1986 | Schaefer |
| 4,628,918 A | 12/1986 | Johnson, Jr. |
| 4,682,588 A | 7/1987 | Curlee |
| 4,896,660 A | 1/1990 | Scott |
| 4,951,940 A | 8/1990 | Vitello et al. |
| 4,966,136 A | 10/1990 | Bates |
| 4,991,573 A | 2/1991 | Miller |
| 5,063,913 A | 11/1991 | Nyi |
| D325,441 S | 4/1992 | O'Brien et al. |
| 5,152,302 A | 10/1992 | Fareed |
| 5,154,690 A | 10/1992 | Shiono |
| D331,801 S | 12/1992 | Shiono |
| 5,211,623 A | 5/1993 | Sarkozi |
| 5,295,949 A | 3/1994 | Hathaway |
| 5,295,951 A | 3/1994 | Fareed |
| D346,245 S | 4/1994 | Krent et al. |
| 5,329,941 A | 7/1994 | Bodine, Jr. |
| 5,372,575 A | 12/1994 | Sebastian |
| 5,375,262 A | 12/1994 | Carter |
| 5,383,844 A | 1/1995 | Munoz et al. |
| 5,403,268 A | 4/1995 | Clement |
| 5,423,333 A | 6/1995 | Jensen et al. |
| 5,445,647 A | 8/1995 | Choy |
| 5,464,384 A | 11/1995 | Cromartie |
| D369,660 S | 5/1996 | Myoga |
| 5,560,041 A | 10/1996 | Walker |
| 5,569,172 A * | 10/1996 | Padden .......... A61F 5/3753 128/878 |
| 5,591,121 A | 1/1997 | Cantrell |
| 5,836,904 A | 11/1998 | Cooper |
| 5,893,871 A | 4/1999 | Tanaka |
| 5,921,949 A | 7/1999 | Dray |
| 5,924,120 A | 7/1999 | Razdan et al. |
| 5,925,010 A | 7/1999 | Caprio, Jr. |
| 6,007,508 A | 12/1999 | Reinhardt et al. |
| D422,362 S | 4/2000 | Ames |
| 6,077,241 A | 6/2000 | Fareed |
| 6,077,242 A | 6/2000 | Falk et al. |
| 6,120,472 A | 9/2000 | Singer, Jr. |
| 6,149,617 A | 11/2000 | McNally et al. |
| 6,244,997 B1 | 6/2001 | Cook |
| 6,352,074 B1 | 3/2002 | Okada |
| 6,361,549 B1 | 3/2002 | Asatourian et al. |
| D455,213 S | 4/2002 | Weaver, II et al. |
| 6,398,749 B1 | 6/2002 | Slautterback |
| 6,402,712 B1 | 6/2002 | Gauvry |
| 6,407,212 B1 | 6/2002 | Morgenthaler et al. |
| D462,772 S | 9/2002 | Lamping et al. |
| 6,478,760 B2 | 11/2002 | Darcey |
| 6,485,448 B2 | 11/2002 | Lamping et al. |
| D473,656 S | 4/2003 | Miros et al. |
| 6,592,539 B1 | 7/2003 | Einarsson et al. |
| 6,659,971 B2 | 12/2003 | Gaylord |
| 6,691,327 B1 | 2/2004 | Meyer |
| 6,711,750 B1 | 3/2004 | Yoo |
| D488,253 S | 4/2004 | Chen |
| D488,523 S | 4/2004 | Hamlin |
| 6,755,800 B2 | 6/2004 | Weaver, II et al. |
| D494,324 S | 8/2004 | Mundy et al. |
| D500,137 S | 12/2004 | Hely |
| 6,852,088 B2 | 2/2005 | Gaylord |
| 6,863,657 B1 | 3/2005 | Clements et al. |
| D503,806 S | 4/2005 | Williams |
| 6,932,781 B2 | 8/2005 | Itoi |
| 7,081,101 B1 | 7/2006 | Sawa |
| D527,108 S | 8/2006 | Krahner |
| D532,523 S | 11/2006 | Krahner et al. |
| D533,668 S | 12/2006 | Brown |
| 7,189,213 B1 | 3/2007 | Weber |
| D545,565 S | 7/2007 | Newman et al. |
| 7,244,239 B2 | 7/2007 | Howard |
| D550,847 S | 9/2007 | Kixmiller |
| D571,016 S | 6/2008 | Matthews |
| 7,393,334 B2 | 7/2008 | Tarnai |
| D580,063 S | 11/2008 | Lin et al. |
| D580,065 S | 11/2008 | Lin et al. |
| D580,554 S | 11/2008 | Lin et al. |
| D580,556 S | 11/2008 | Lin et al. |
| D582,994 S | 12/2008 | Ulichney et al. |
| D582,995 S | 12/2008 | Ulichney et al. |
| D594,634 S | 6/2009 | Dolby |
| D596,746 S | 7/2009 | Reinhardt et al. |
| 7,563,236 B2 | 7/2009 | Kazmierczak et al. |
| D598,115 S | 8/2009 | Reinhardt et al. |
| D598,555 S | 8/2009 | Chen |
| 7,637,883 B2 | 12/2009 | Nyi |
| 7,640,610 B2 | 1/2010 | Mervar |
| 7,730,550 B2 | 6/2010 | Chiang |
| 7,740,645 B2 | 6/2010 | Babaev |
| 7,749,179 B2 | 7/2010 | Hargrave et al. |
| D623,757 S | 9/2010 | Chiang |
| D623,759 S | 9/2010 | Chiang |
| D626,245 S | 10/2010 | Sagnip et al. |
| D630,333 S | 1/2011 | Chiang |
| 7,951,104 B2 | 5/2011 | Rodgers, Jr. et al. |
| D642,280 S | 7/2011 | Goumas |
| 8,016,780 B1 | 9/2011 | Sickles |
| 8,043,241 B2 | 10/2011 | Goumas |
| D654,182 S | 2/2012 | Chiang |
| 8,109,273 B2 | 2/2012 | Golden et al. |
| 8,118,765 B2 | 2/2012 | Magnusson |
| D667,956 S | 9/2012 | Chiang |
| 8,273,040 B1 | 9/2012 | Morrow |
| D671,690 S | 11/2012 | Brady et al. |
| 8,523,793 B1 | 9/2013 | Waldon, Sr. |
| D693,065 S | 11/2013 | Cook |
| D695,902 S | 12/2013 | Daniels et al. |
| 8,628,488 B2 | 1/2014 | Serola |
| 8,671,162 B2 | 3/2014 | Kline et al. |
| D703,824 S | 4/2014 | Ferguson, Jr. |
| D711,050 S | 8/2014 | Ebrahimi |
| D713,047 S | 9/2014 | Eriksson |
| 8,821,425 B2 | 9/2014 | Cox |
| D720,860 S | 1/2015 | Meyer et al. |
| D728,805 S | 5/2015 | Tanaka et al. |
| D728,806 S | 5/2015 | Cox |
| D734,563 S | 7/2015 | Daniel |
| D746,997 S | 1/2016 | Higgins |
| D750,261 S | 2/2016 | Kusmirek et al. |
| 9,320,639 B2 | 4/2016 | Serola |
| D767,772 S | 9/2016 | Jiminez |
| D767,773 S | 9/2016 | Jiminez |
| D778,506 S | 2/2017 | Matfus et al. |
| D800,323 S | 10/2017 | Cox |
| D800,324 S | 10/2017 | Cox |
| D800,326 S | 10/2017 | Cox |
| D802,154 S | 11/2017 | Ceccarelli |
| D802,778 S | 11/2017 | Lo |
| D804,680 S | 12/2017 | Bledsoe et al. |
| D841,439 S | 2/2019 | Merten et al. |
| D849,255 S | 5/2019 | Colleran |
| 10,398,585 B2 | 9/2019 | Cox |
| 2002/0147421 A1 | 10/2002 | Darcey |
| 2002/0169407 A1 | 11/2002 | Glinsboeckel |
| 2003/0187373 A1 | 10/2003 | Gaylord |

(56) References Cited

U.S. PATENT DOCUMENTS

| | | |
|---|---|---|
| 2004/0129278 A1 | 7/2004 | Ltoi |
| 2005/0010147 A1* | 1/2005 | Kazmierczak ........ A61F 5/3753 602/4 |
| 2005/0055775 A1 | 3/2005 | Gourd |
| 2005/0132465 A1 | 6/2005 | Kathumbi-Jacknson et al. |
| 2005/0240134 A1 | 10/2005 | Brown |
| 2005/0273026 A1 | 12/2005 | Howard |
| 2006/0026730 A1 | 2/2006 | Terczak |
| 2007/0077393 A1 | 4/2007 | Chiang et al. |
| 2007/0161932 A1 | 7/2007 | Pick et al. |
| 2008/0188788 A1 | 8/2008 | Serola |
| 2009/0287124 A1 | 11/2009 | Shmidman |
| 2010/0042031 A1 | 2/2010 | Anglada |
| 2010/0152635 A1 | 6/2010 | Borden |
| 2010/0210985 A1 | 8/2010 | Kuorak et al. |
| 2011/0009795 A1 | 1/2011 | Graham |
| 2011/0021958 A1 | 1/2011 | Lynds |
| 2011/0040227 A1 | 2/2011 | Magri |
| 2011/0179542 A1 | 7/2011 | Khuong et al. |
| 2011/0192403 A1 | 8/2011 | Goumas |
| 2012/0010546 A1 | 1/2012 | Sotereanos et al. |
| 2012/0096616 A1 | 4/2012 | Fisher et al. |
| 2012/0150083 A1 | 6/2012 | McCune et al. |
| 2012/0209159 A1 | 8/2012 | Fout |
| 2012/0277649 A1 | 11/2012 | Matsuo et al. |
| 2012/0289875 A1 | 11/2012 | Matsuo et al. |
| 2013/0064345 A1* | 3/2013 | Kaska ................... A61B 6/505 378/62 |
| 2013/0131568 A1 | 5/2013 | Golden et al. |
| 2013/0160176 A1 | 6/2013 | Magri |
| 2014/0188024 A1 | 7/2014 | Cox |
| 2014/0358052 A1 | 12/2014 | Cox |
| 2015/0073317 A1 | 3/2015 | Cox |
| 2016/0000612 A1 | 1/2016 | Cox |

FOREIGN PATENT DOCUMENTS

| | | |
|---|---|---|
| EP | 0362528 A1 | 4/1990 |
| EP | 0904752 A1 | 3/1999 |
| EP | 2097113 A2 | 9/2009 |
| JP | 2005245611 A | 9/2005 |
| JP | 2010508072 A | 3/2010 |
| KR | 100883324 B1 | 2/2009 |
| KR | 1020090092772 A | 9/2009 |
| WO | 2008051640 A2 | 5/2008 |
| WO | 2008051640 A3 | 7/2008 |
| WO | 2014/106228 A1 | 7/2014 |
| WO | 2014/194221 A1 | 12/2014 |

OTHER PUBLICATIONS

"Final Office Action received for U.S. Appl. No. 13/905,337 dated Apr. 21, 2016.", 30 Pages.

"Final Office Action Received for U.S. Appl. No. 13/905,337, dated Apr. 19, 2018, 23 Pages."

"Flexxline Knee Compression Sleeve, reviewed Mar. 20, 2016, [online], [site visited Oct. 26, 2016]. Available from Internet, <URL:http://www.flexxline.com/collections/leg/products/knee-compression-sleeve>".

"International Preliminary Report on Patentability received for International Patent Application Serial No. PCT/US2014/040279 dated Dec. 10, 2015.", 10 Pages.

"International Preliminary Report received for International Application No. PCT/US2013/078429 dated Jul. 9, 2015, 10 pages.", 10 pages.

"International Preliminary Report received for International Application No. PCT/US2014/040279 dated Dec. 10, 2015,", 10 pages.

"Non-Final Office Action received for U.S. Appl. No. 13/905,337 dated Dec. 27, 2016.", 33 Pages.

"Non-Final Office Action received for U.S. Appl. No. 13/905,337 dated Jul. 3, 2017.", 40 Pages.

"Non-Final Office Action received for U.S. Appl. No. 13/905,337 dated Mar. 13, 2015.", 41 Pages.

"Non-Final Office Action received for U.S. Appl. No. 29/657,371 dated Nov. 5, 2019."

"Notice of Allowance Received for U.S. Appl. No. 13/905,337, dated Apr. 23, 2019, 8 pages", dated Dec. 4, 2014.

13867118.5 , "European Search Report for Application No. EU13867118.5; dated Aug. 5, 2016", dated Aug. 5, 2016.

PCT/US2013/078429 , "Written Opinion and International Search Report for PCT/US2013/078429 (dated Apr. 3, 2014)", dated Apr. 3, 2014, 11.

PCT/US2014/040279 , "Written Opinion of the International Searching Authority for PCT/US2014/040279 (dated Oct. 1, 2014)", dated Oct. 1, 2014, 12.

\* cited by examiner

SHOULDER AND ARM RESTRAINT

CROSS-REFERENCE TO RELATED APPLICATIONS

This application is a continuation application of U.S. patent application Ser. No. 13/905,337, filed May 20, 2013, now U.S. Pat. No. 10,398,585, and is a continuation of U.S. patent application Ser. No. 14/444,733, filed Jul. 28, 2014, which is a continuation application of U.S. patent application of Ser. No. 13/731,289, filed Dec. 31, 2012, now U.S. Pat. No. 8,821,425, the entire disclosure of which is incorporated herein by reference.

FIELD OF THE INVENTION

The present invention relates generally to therapeutic devices. More specifically, the invention relates to a therapeutic device for recuperative support following surgical repair to a human arm or shoulder. In preferred embodiments the invention relates to a device that aids in restraining movement of a human arm or shoulder by maintaining the arm and shoulder in a fixed yet comfortable position for extended periods of time.

BACKGROUND

Following an operation or injury to an arm or shoulder it is often necessary to immobilize the afflicted arm in a substantially stationary position where the upper arm is slightly elevated and where the forearm is slightly away from the body. Over the years several types of devices were developed to accomplish this. Early devices included metallic arm supports and plaster casts which greatly decreased patient mobility and greatly increased patient discomfort.

Later devices such as those discussed in U.S. Pat. Nos. 4,896,660; 7,244,239; 8,109,273 and other patents show more pliable and flexible devices that incorporate foam, pillows, straps and harnesses. Although there are a plethora of devices containing various soft components and architectures for stabilizing or restraining a human shoulder and arm, most are still quite bulky, overly complicated and uncomfortable for the wearer.

For example, the device discussed in U.S. Pat. No. 4,896,660 comprises multiple foam components that are connected by hook and loop fasteners and straps. The components are positioned such that it is likely impossible for a recovering surgical patient to put the device on and off without assistance. In addition the device has the affected arm extending from the body in an unprotected, spar-like manner where it is easily caught on obstacles such as doorways, furniture and the like.

Other devices such as those discussed in U.S. Pat. Nos. 8,109,273 and 7,244,239 encase the forearm and/or upper arm in a rigid orthotic (U.S. Pat. No. 8,109,273) or a sling (U.S. Pat. No. 7,244,239). Patients report that such devices are uncomfortable due to heat build-up and/or the formation of pressure points.

Additional patient complaints relate to the shoulder strap that typically accompanies such devices. Restraint devices typically incorporate some form of a strap that extends around the neck to rest against the neck or more preferably on the opposite shoulder. Typically these straps are padded as in U.S. Pat. No. 7,244,239 and/or incorporate loops or other tension reducing devices to increase comfort for the user. Unfortunately, such straps tend to "creep" from the shoulder toward the side of the neck where the weight of the supported arm becomes more focused. This results in patient discomfort. The discomfort can lead to the patient shrugging the injured shoulder in an effort to move the strap to a more comfortable position which moves the shoulder and arm. Some devices, such as the '239 device attempt to address this problem by fixing a shoulder strap to a torso strap to prevent shoulder strap movement. Unfortunately, this architecture complicates use of the device, often to the extent that a patient needs help putting on and removing the device.

The difficulties and shortcomings discussed above are not intended to be exhaustive, but rather are among many which may tend to reduce the effectiveness and patient satisfaction with existing devices. Perhaps, more importantly, the human body is a very dynamic system. Treatments, braces, and straps that provide relief for one patient often do not provide relief for another, which is one reason there is such a large number of orthopedic devices on the market for all types of orthopedic conditions. Accordingly, there is a continuing need for new and innovative orthopedic devices to provide treatment and relief to those patients that do not respond to known treatment methods.

SUMMARY

In one aspect, the invention is a shoulder restraint device comprising a pillow having a top face, a bottom face, a lateral face, a medial face, an anterior face, and a posterior face. The medial face is generally concave and the lateral face has a proximal border and a distal border that generally defines the proximal to distal "height" of the device. The device also comprises a padded forearm support extending along a portion of the pillow lateral face intermediate the anterior face and the posterior face. The padded forearm support is separate from but permanently attached to the pillow lateral face proximate the distal border of the pillow lateral face. The device also comprises a forearm strap releaseably connected to the pillow and a shoulder strap having a first end connected to an anterior point on the pillow and a second end connected to a posterior point on the pillow. The shoulder strap has a length sufficient to traverse the opposite shoulder of a user and preferably has a scalloped portion that traverses the clavicle region of the opposite shoulder.

Another aspect of the invention encompasses a method for restraining the movement of an arm and a shoulder joint. The method comprises the step of providing a restraint device such as the one described in the preceding paragraph and positioning the pillow (and the overall device) to rest against a human torso. The scalloped portion of the shoulder strap is positioned to traverse the clavicle region of the opposite shoulder. The forearm of the user is then positioned to rest upon the padded forearm support and secured in place by engaging the forearm strap with the padded forearm support and pillow.

The foregoing and other objects are intended to be illustrative of the invention and are not meant in a limiting sense. Many possible embodiments of the invention may be made and will be readily evident upon a study of the following specification and accompanying drawings comprising a part thereof. Various features and subcombinations of invention may be employed without reference to other features and subcombinations. Other objects and advantages of this invention will become apparent from the following description taken in connection with the accompanying drawings, wherein is set forth by way of illustration and example, an embodiment of this invention and various features thereof.

BRIEF DESCRIPTION

These and other more detailed and specific features of the present invention are more fully disclosed in the following specification, reference being had to the accompanying drawings, in which.

DETAILED DESCRIPTION

In the following description, for purposes of explanation, numerous details are set forth, such as device configurations and possible movements, to provide an understanding of one or more embodiments of the present invention. Furthermore, the following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

While the invention is described with respect to various embodiments thereof, it will be understood by those skilled in the art that various changes in detail may be made therein without departing from the spirit, scope, and teaching of the invention. Accordingly, the invention herein disclosed is limited only as specified in the claims.

Figure 1:
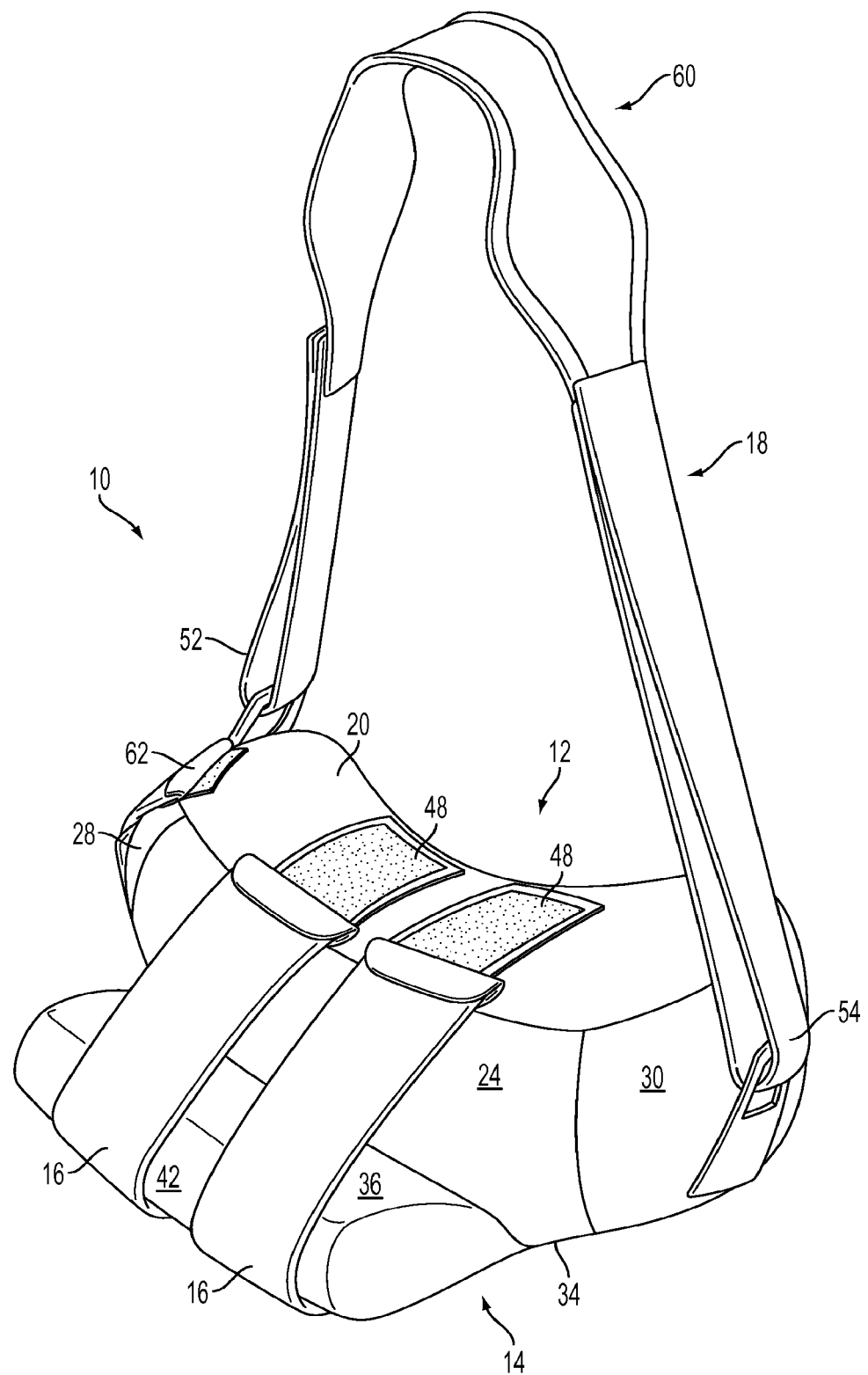
FIG. 1 is a perspective view of a restraint device according to the invention.
Figure 2:
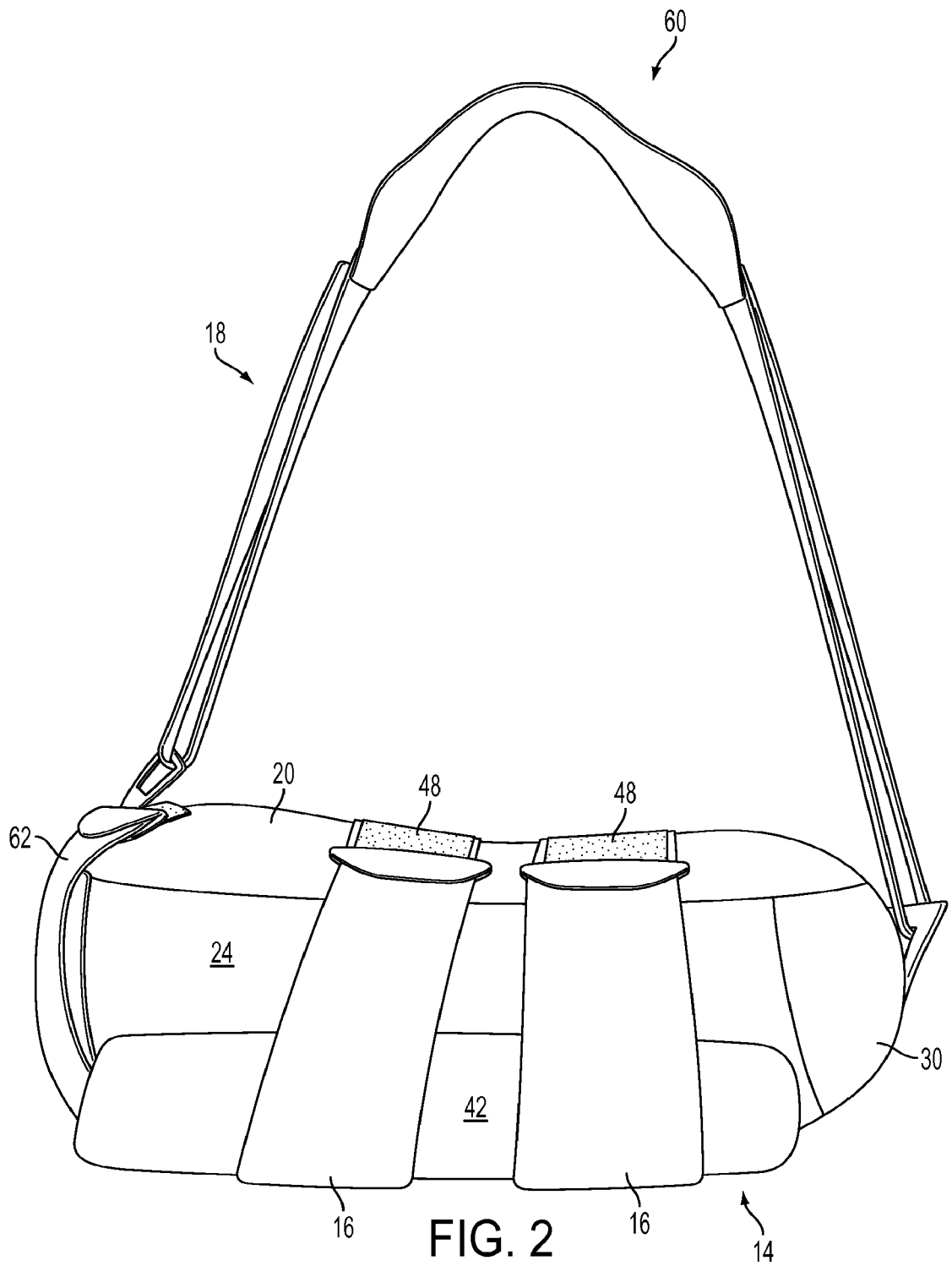
FIG. 2 is a view of the lateral side of a restraint device according to the invention.

Referring now to the drawings in detail, where like numerals refer to like parts or elements, there is shown in FIG. 1 one embodiment of a shoulder and arm stabilizing restraint 10 according to the invention. Although the restraint can be considered to be a single unit this detailed description discusses the various components of the device separately as an aid in understanding the invention.

In one embodiment the restraint 10 comprises a pillow 12, a padded forearm support 14, at least one forearm strap 16 and a shoulder strap 18. The pillow 12 is a generally oblong, flexible, soft, and pliant support that is formed of fabric that surrounds and encases a formed or molded and compressible foam. Alternatively, the fabric of the pillow 12 could surround and encase filler such as cotton batting, polyester filament, latex shards, buckwheat hulls, polymer spheres, or similar fillers. In other embodiments, the pillow 12 could consist of a formed or molded foam that is not encased by fabric but has stable attachments (e.g., polymer tabs or tags) suitable for attaching the other listed components. The pillow 12 utilized in the practice of the invention may be formed using any known and suitable method for producing pillows.

Those skilled in the art recognize that there may be some differences from pillow to pillow depending on how the pillow utilized in the invention is made. For example, the pillows 12 discussed herein are described in terms of having a plurality of "faces" (e.g., top face, bottom face, etc.). Pillows made from formed or molded foam will have typically have rather smooth and flat faces that intersect with each other in generally linear and angular fashion. In contrast, pillows made from fabric encased with filler (e.g., "stuffed" pillows) will have more rounded faces that transition from one to the other over more rounded edges and seams.

For purposes of this discussion it is assumed that the pillow 12 is formed by sewing one or more panels of fabric together to create a "stuffed" pillow of the form generally depicted in FIG. 1 where faces and angles are somewhat rounded for patient comfort. Thus, directional and architectural terms such as "face" or "parallel" are used in a general sense rather than a precise geometrical sense.

Figure 8:
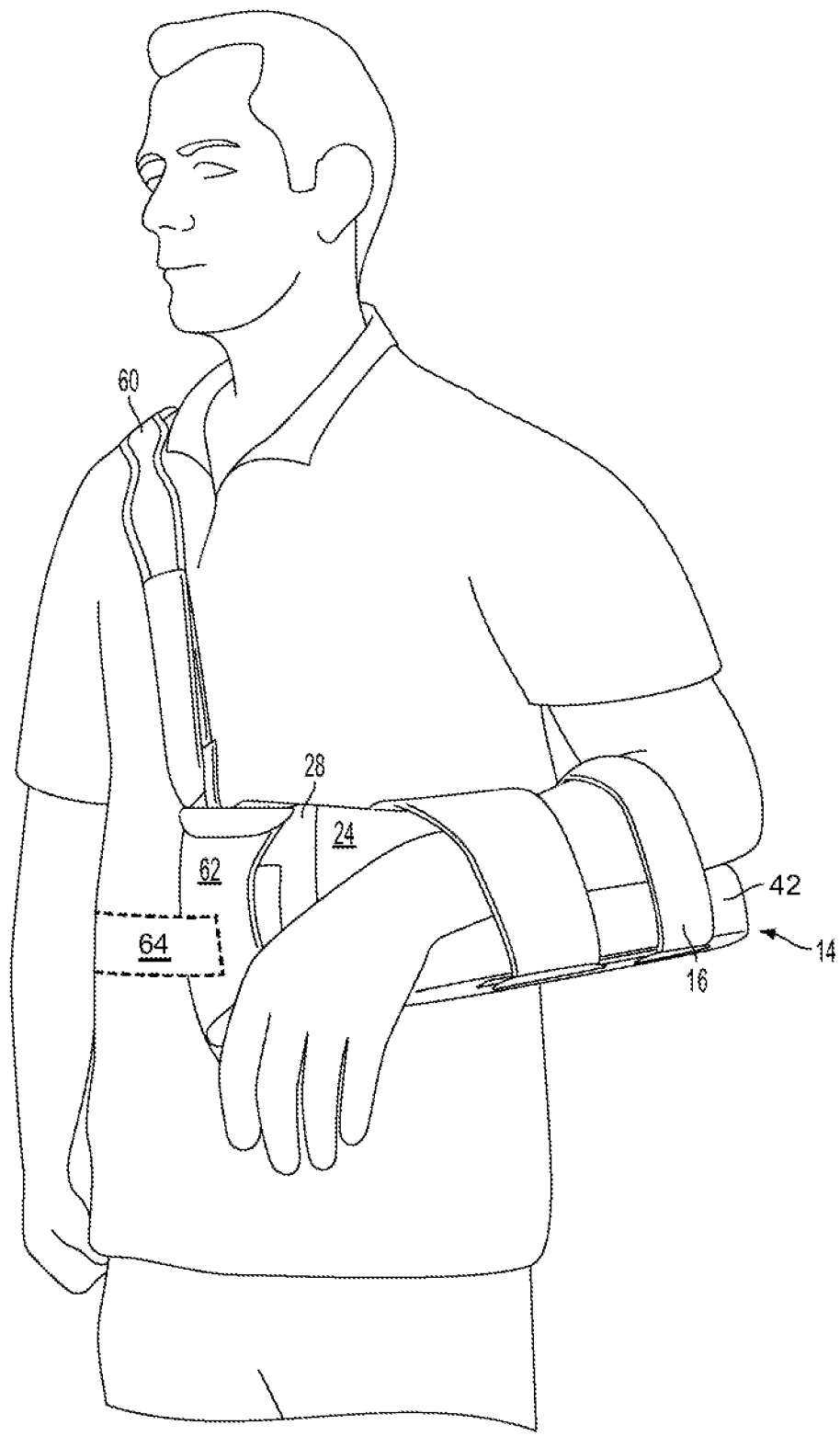
FIG. 8 is an illustration of a human using a restraint device according to the invention.
Figure 9:
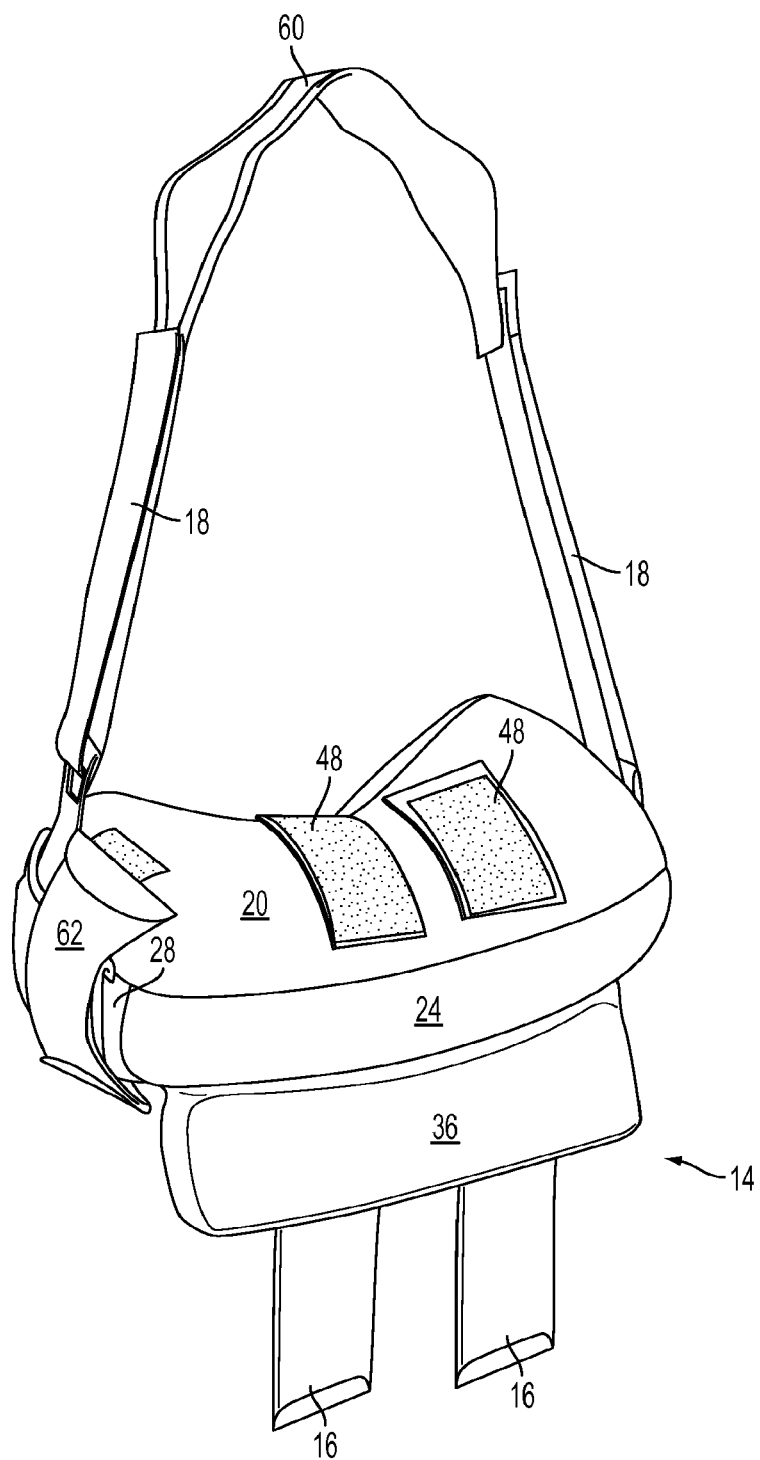
FIG. 9 is a perspective view of a restraint device according to the invention illustrating the device as it would appear hanging loose without the forearm straps engaged.

FIG. 1 illustrates one pillow 12 that may be used in the practice of the invention. Note that this pillow is generally best suited for use in securing the left arm and shoulder as shown in FIG. 8. Those skilled in the art can adapt the invention as necessary for use with a right arm and shoulder.

The pillow 12 has a top face 20, a bottom face 22, a lateral face 24, a medial face 26, an anterior face 28, and a posterior face 30. The top face 20 is separated from the bottom face 22 by a distance. The distance between top face 20 and the bottom face 22 is defined by the proximal-to-distal width "A" of the medial face 26 (FIG. 3) and the proximal-to-distal width "B" of the lateral face 24 (FIG. 4). In most instances the widths "A" and "B" will be roughly the same such that top face 20 and bottom face 22 are roughly parallel to each other. However, some deviation between "A" and "B" will not alter the practice of the invention.

In preferred embodiments the distance "B" is sufficient to allow a portion of the pillow lateral face 24 to serve as a surface against which the forearm of the user may rest as shown in FIG. 8. In other words, the distance "B" should be sufficient that when the forearm support 14 is attached to the pillow, the lateral face 24 forms a wall preventing the forearm of the user from moving medially toward the body of the user.

Figure 7:
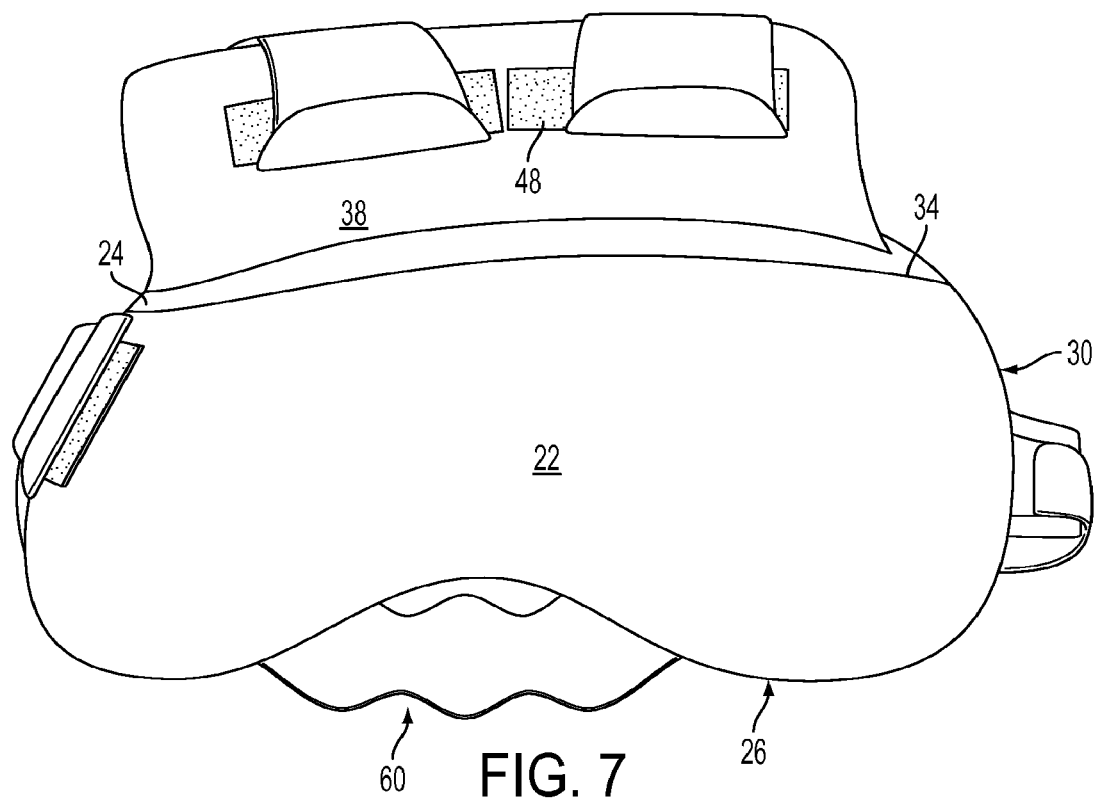
FIG. 7 is a bottom view of a restraint device according to the invention.

The medial face 26 is generally concave as shown in FIG. 7 to conform to the general shape of a human torso. The anterior to posterior length of the pillow 12 and the degree of concavity for medial face 26 can be altered to fit various sized individuals.

Figure 3:
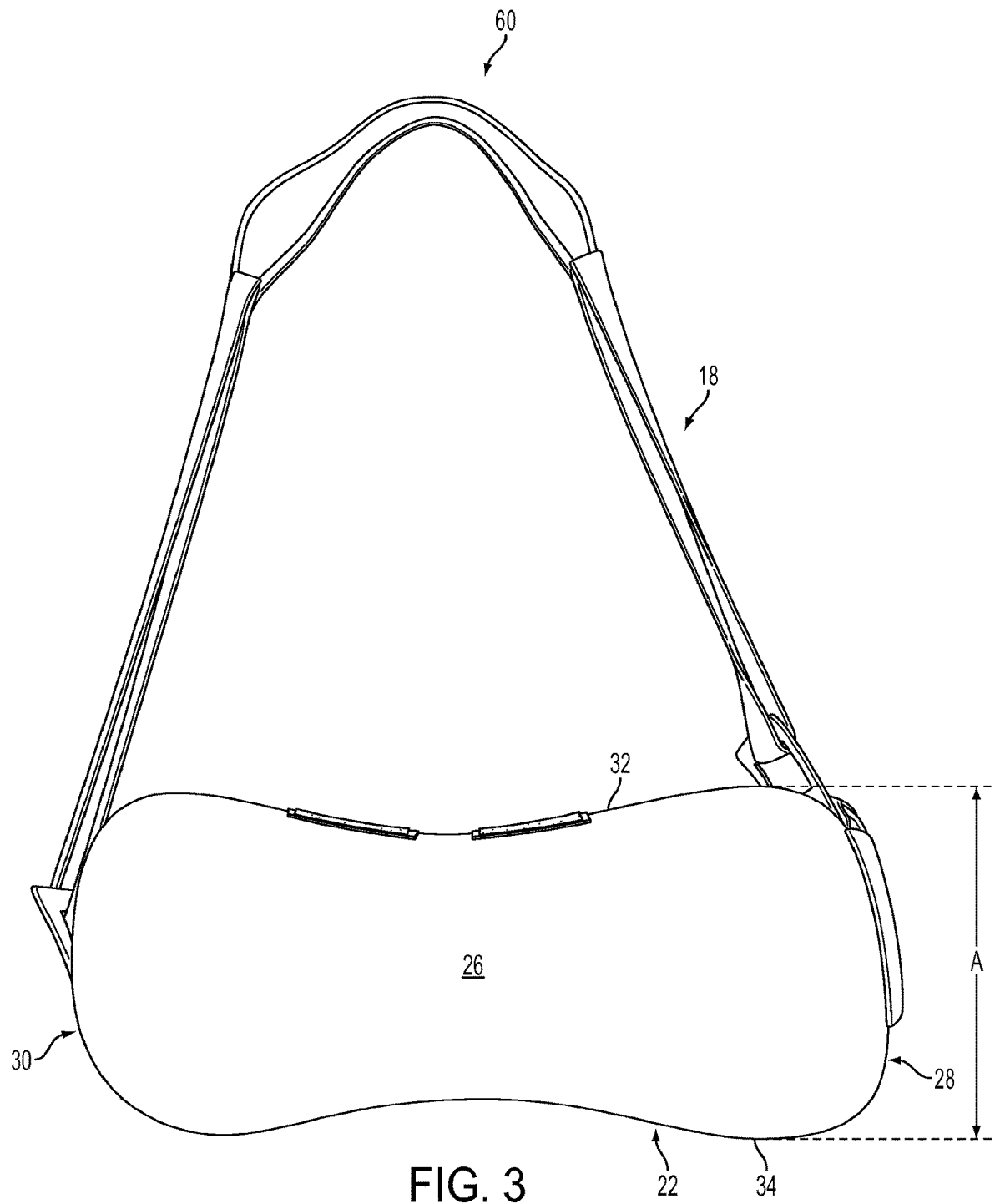
FIG. 3 is a view of the medial side of a restraint device according to the invention.
Figure 4:
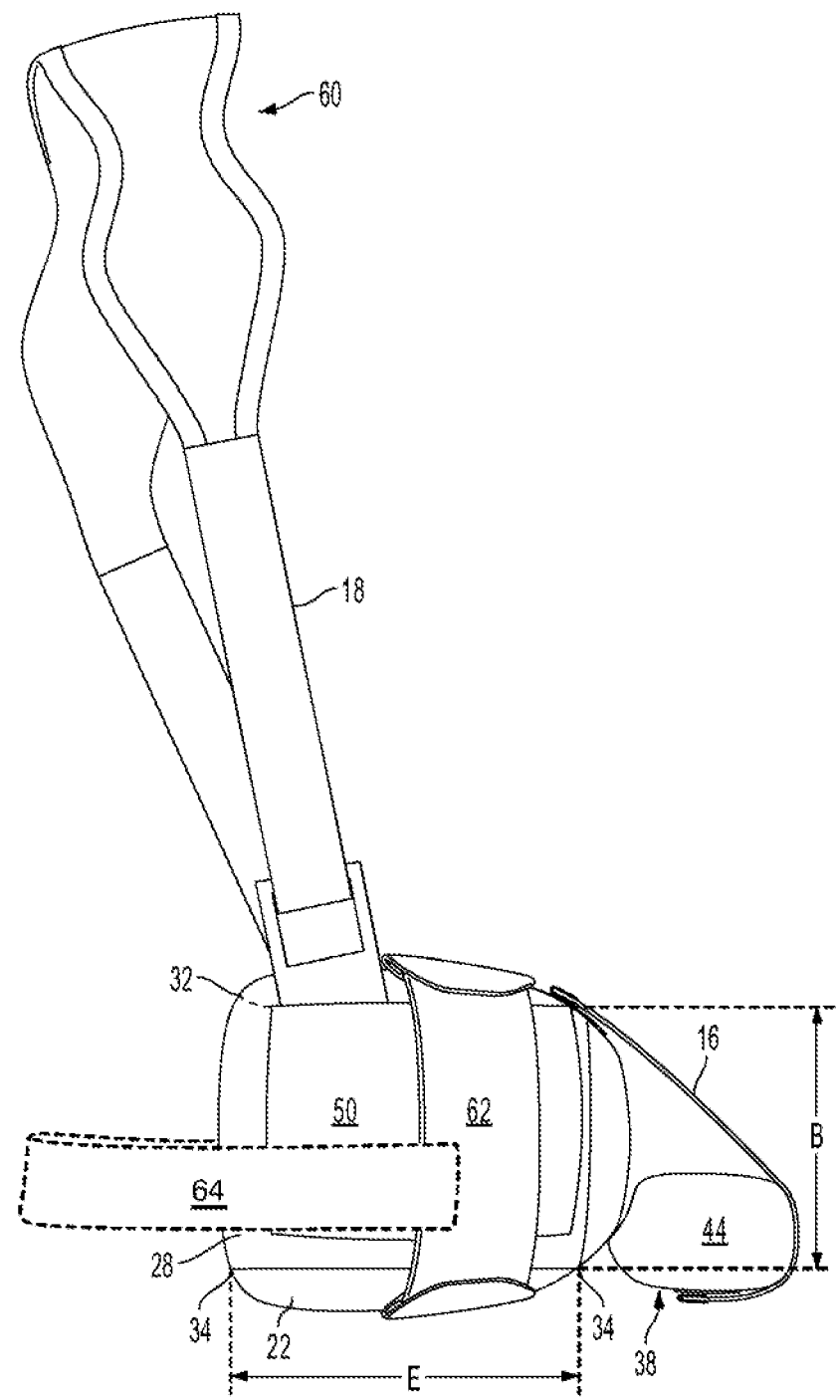
FIG. 4 is a view of the anterior side of a restraint device according to the invention.

The pillow medial face 26 is defined by a proximal border 32 and a distal border 34, FIG. 3. The pillow lateral, anterior and posterior faces have similar proximal and distal borders.

Figure 5:
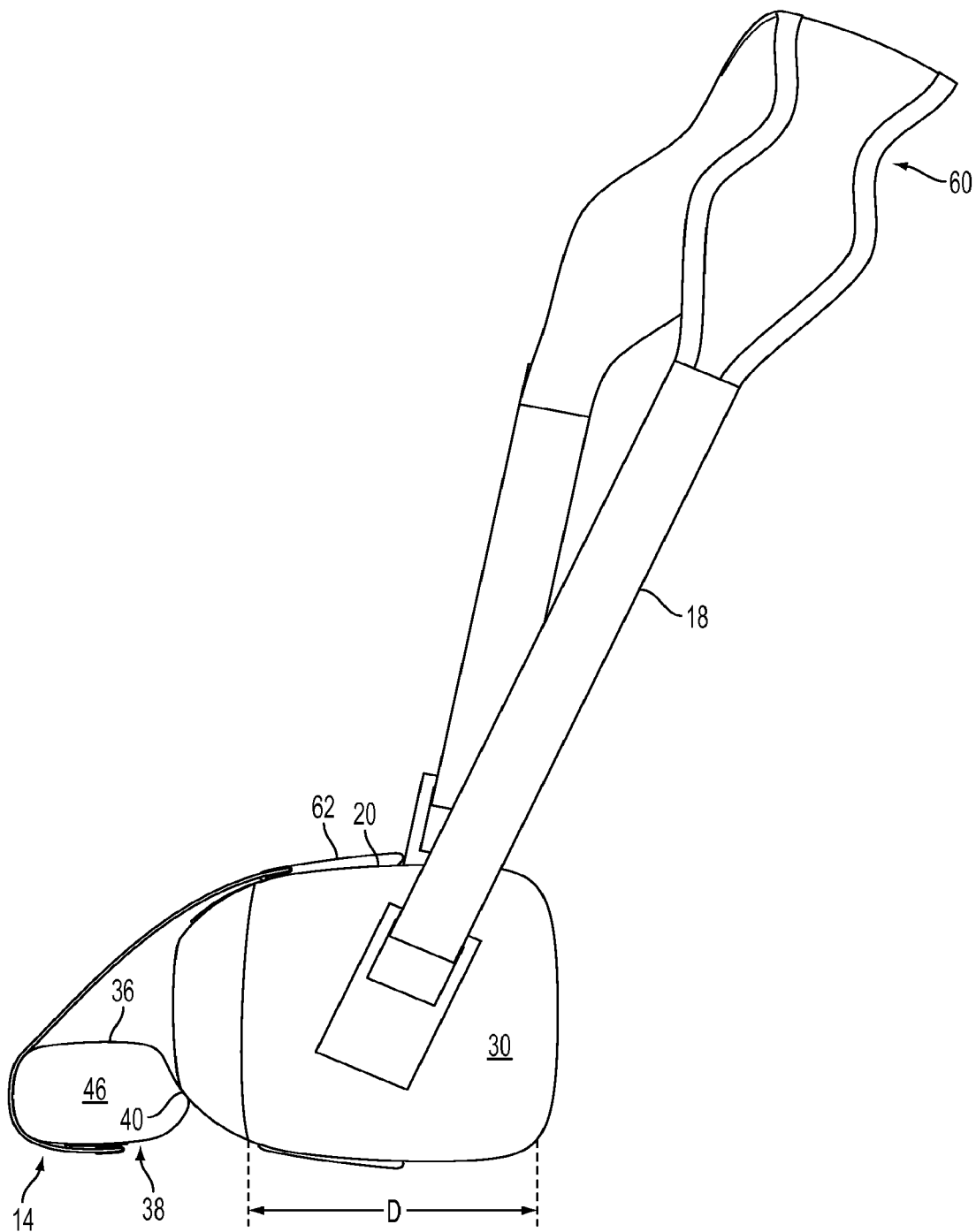
FIG. 5 is a view of the posterior side of a restraint device according to the invention.
Figure 6:
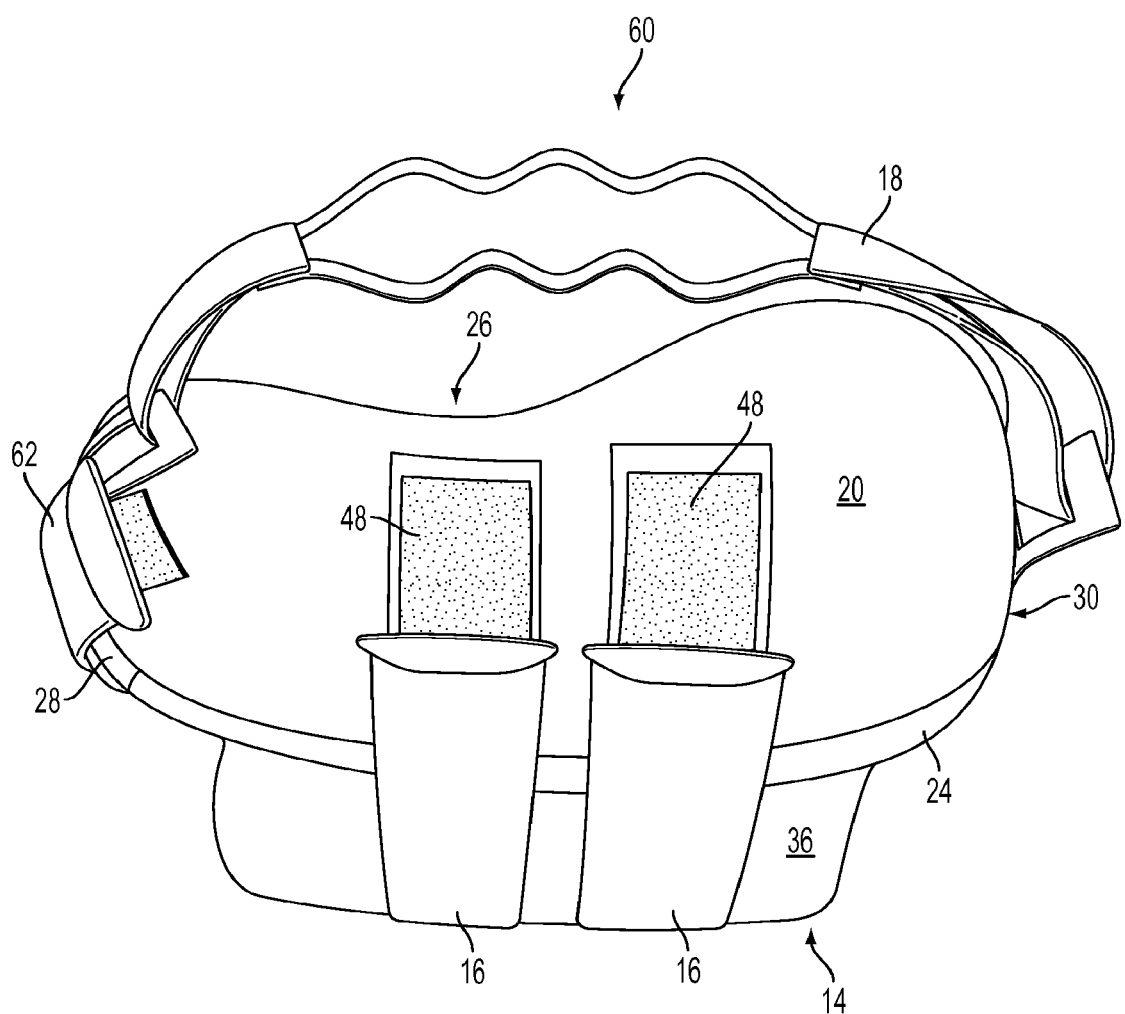
FIG. 6 is a top view of a restraint device according to the invention.

In one preferred embodiment the posterior portion of the pillow 12 is larger than the anterior portion as shown in FIG. 6 giving the pillow a slight kidney-bean shape. Specifically, in this embodiment the pillow anterior face 28 is smaller than the pillow posterior face 30. More specifically, the medial to lateral width "D" (FIG. 5) of the posterior face 30 is greater than the medial to lateral width "E" (FIG. 4) of the anterior face 28. One benefit of such an arrangement is that it places the arm and shoulder in a somewhat neutral position where the forearm of the user is substantially parallel to the body's sagittal plane.

The device 10 further comprises a padded forearm support 14 permanently connected to and extending along a portion of the pillow lateral face 24 intermediate the pillow anterior face 28 and the pillow posterior face 30. The padded forearm support 14 is similar to the pillow 12 in that it can be formed of the same materials and in the same fashion (e.g., a "stuffed" fabric or foam covered fabric).

Likewise, the padded forearm support 14 is defined by a forearm support top face 36, a forearm support bottom face 38, a forearm support medial face 40, a forearm support lateral face 42, a forearm support anterior face 44, and a forearm support posterior face 46. In preferred embodiments the forearm support medial face 40 abuts the pillow lateral face 24 and is contoured to match the contour of the lateral face 24.

For example, if the pillow 12 is "stuffed" with filler such that the lateral surface 24 is slightly rounded, then the forearm support medial face 40 can be contoured to have a slightly angled curve in it. With a slightly angled curve, the forearm support medial face 40 can rest flush against the lateral surface 24 along its entire length. This arrangement positions the forearm support top face 36 substantially perpendicular to the pillow lateral face 24 when the device is in use. The contouring can take the form of creating a contoured fabric enclosure that is stuffed with filler. Alternatively, and generally preferably, the forearm support 14 is made from a formed or molded compressible foam that can be easily contoured thus increasing manufacturing efficiencies.

In a preferred embodiment the padded forearm support 14 is separate from but permanently attached to the pillow lateral face 24 proximate the distal border 34 of the pillow lateral face 24. The method of permanent attachment can vary depending upon the materials and architecture utilized in the construction of the restraint. In a preferred embodiment that incorporates a pillow 12 and a forearm support 14 that is covered in fabric, the fabric of the forearm support medial face 40 is sewn to the fabric of the pillow lateral face 24. However, glue or other types of permanent attachment can be used as well. For purposes of this discussion a zippered attachment is also considered a permanent attachment due to the mechanical difficulty and manual dexterity required to engage and disengage a zipper.

Permanent attachment of the forearm support 14 to the pillow 12 prevents the forearm support 14 from being accidentally dislodged during use as can happen with devices that utilize hook and loop fasteners to connect forearm supports to torso pillows.

As noted previously, attaching the padded forearm support 14 proximate the distal border 34 of the lateral face 24 provides a "shelf" upon with the user's forearm may comfortably rest and a "retaining wall" that prevents medial movement of the forearm which in turn helps isolate the shoulder joint.

Fabric covers for both the forearm support 14 and pillow 12 can have portals (not shown) that allow the user to change the padding level of the forearm support 14 or pillow 12. For example, one of the faces of the forearm support 14 or pillow 12 can have a zipper (not shown) that allows access to the interior of the forearm support 14 covering or pillow 12 for purposes of adding, removing or exchanging padding.

As noted above, some prior art devices utilize a sling or otherwise fully encase the forearm and/or upper arm in fabric or formed polymer to immobilize the arm and shoulder. Some patients find such sling arrangements uncomfortable because the slings trap heat and prevent air flow. Slings also tend to hold the arm tightly which can cause discomfort.

In contrast, the stabilizing restraint 10 comprises at least one forearm strap 16 that restrains the arm to maintain forearm placement on the forearm support top face. In a preferred embodiment the forearm strap 16 is made of an elastic material and preferably a soft, pliant fabric such as a jersey knit to maximize user comfort. Other types of straps such as thin polymer sheeting or leather can be used as well. One end of the forearm strap 16 is connected to the forearm support 14 and the other end is connected to the pillow 12.

The points of attachment and the manner of attachment for the forearm strap 16 can vary. Generally speaking, the primary requirement is that the forearm strap 16 traverse the arm of the user in a way to maintain forearm placement as shown in FIG. 8. The forearm strap 16 can be connected using several combinations of forearm support faces and pillow faces. In preferred embodiments the forearm strap 16 is connected to the forearm support bottom face 38 and extends over the forearm support lateral face 42 to attach to the pillow top face 20 as shown in FIG. 1 or a proximal point on the pillow lateral face 24.

The forearm strap 16 is preferably releasably attached to either the forearm support 14 or the pillow 12 or both. Alternatively, the forearm strap 16 can be permanently attached to either the forearm support 14 or the pillow 12. In a preferred embodiment of the invention, the forearm strap 16 is either permanently attached (e.g., sewn) or releaseably attached (e.g., loop and hook fastener 48) to the forearm support bottom face 38 and releasably attached to the pillow top face 20.

As noted previously, using slings or wide straps to restrain a forearm can cause discomfort for a user. Thus, in preferred embodiments a plurality of forearm straps 16 are used to secure the forearm of the user in the angle created by the pillow lateral face 24 and the forearm support top face 36. Each of the forearm straps 16 are separated by a distance thereby exposing a portion of the arm representing the diaphysis of the radius and ulna.

In other words, the forearm is held in place by discrete straps that keep the arm and shoulder restrained yet minimize contact with the arm while providing air circulation around the arm for maximum comfort.

The forearm support 14 and pillow 12 are secured to the user's body by the use of straps. One such strap is a shoulder strap 18 such as those commonly used in other restraint devices. The shoulder strap 18 is defined by a first end 52 and a second end 54. The first end 52 is connected to an anterior point of the pillow 12. The exact point of attachment is not critical although attachment to a point proximate the pillow anterior face 28 is recommended. Similarly, the second end 54 is connected to a posterior point of the pillow 12. The exact point of attachment is not critical although attachment to a point proximate the pillow posterior face 30 is recommended.

The shoulder strap 18 can be connected to the pillow 12 by any conventional means known in the art (e.g., D-ring and quick-clips) and is preferably adjustable as is known in the art. The shoulder strap 18 should be of a length sufficient to extend around the neck of the user and traverse the opposite shoulder of the user, particularly the area around the clavicle.

Typical shoulder straps tend to slide toward the neck of a user during use which can cause discomfort to the user. One structural remedy for this is to add a waist strap and fix the shoulder strap to the waist strap as shown in U.S. Pat. No. 7,244,239. Although such an arrangement aids in preventing creep of the shoulder strap toward the neck, the arrangement of straps makes it difficult for a user with one good arm to put the device on and secure it properly.

The current invention addresses the issue of shoulder strap creep without resorting to a complicated harness. The restraint device of the current invention utilizes a traditional two-connection strap that slides easily over the head of a user. However, in a preferred embodiment, the shoulder strap 18 has a scalloped portion 60 intermediate the first 52 and second 54 ends of the strap. During use the scalloped portion 60 is positioned such that it traverses the clavicle area of the opposite shoulder. The scalloped portion 60 is preferably wider than the remainder of the shoulder strap 18. The scalloped portion 60 may be integral with the strap 18 or it may be constructed to be a sleeve that slides along the length of the strap 18.

The curved edges of the scalloped portion 60 conform to the natural curve of the shoulder, specifically the clavicle area, thus creating more contact between the strap and the shoulder. The difference in grip can be demonstrated as follows. Place a hand, palm down with thumb flush against side of the palm, over the opposite clavicle. Move the hand back and forth from the neck to the edge of the shoulder and note the force required to do so.

Now move the thumb away from the palm and position the hand such that the clavicle is now between the outstretched thumb and forefinger—the clavicle is in the web of the hand. Note that the natural curvature of the web of the hand adds grip and almost locks the hand in place. The curves of the scalloped portion 60 can work in a similar fashion to hinder movement of the shoulder strap 18 toward the neck and thus provide greater comfort to the user. Covering the side of the scalloped portion 60 that contacts the shoulder with a fabric having a high coefficient of friction further prevents strap creep.

The stabilizing restraint 10 of the claimed invention can also comprise a waist strap 64 that is similar to those discussed above and shown in other restraint systems. Such a strap would attach to an anterior point on the pillow 12, extend around the body of the user, and attach to a posterior point on the pillow 12.

The stabilizing restraint 10 of the claimed invention can also comprise a hand strap 62 that traverses the pillow anterior face 28 as shown in FIG. 4 and serves to hold the user's hand in a neutral position and/or relieve stress on the user's wrist. The hand strap 62 may be made from the same materials as the forearm strap 48 and is connected to the anterior portion of the pillow 12 in a similar fashion. An optional pouch 50 can be added to the pillow to hold possessions. The pouch 50 can be on any face. In FIG. 4 it is shown on the anterior face 28.

A further aspect of the invention is a method for restraining the movement of an arm or shoulder joint. The steps of this method include providing a pillow 12 having a top face 20, a bottom face 22, a lateral face 24, a medial face 26, an anterior face 28, and a posterior face 30, where the medial face 26 is generally concave to conform to the torso of a user and where the lateral face 24 has a proximal border 32 and a distal border 34.

The method also includes providing a padded forearm support 14 extending along a portion of the pillow lateral face 24 intermediate the anterior face 28 and the posterior face 30. The padded forearm support 14 is preferably separate from but permanently attached to the pillow lateral face 24 proximate the distal border 34 of the pillow lateral face 24.

A shoulder strap 18 is provided. The shoulder strap 18 is as described above and has a first end 52 connected to an anterior point 52 on the pillow 12 and a second end 54 connected to a posterior point 58 on the pillow 12. The shoulder strap 18 is of a length sufficient to traverse the opposite shoulder of a user.

The method continues by positioning the pillow 12 such that the concave medial face 26 of the pillow 12 rests against a human torso; positioning the shoulder strap 18 to traverse the opposite shoulder of a user; positioning the forearm of the user to rest upon the padded forearm support 14; and securing the forearm by engaging a forearm strap 48 that traverses the human forearm and attaches to the forearm support 14 and the pillow 12 as described above.

In the drawings and specification, there have been disclosed typical embodiments on the invention and, although specific terms have been employed, they have been used in a generic and descriptive sense only and not for purposes of limitation, the scope of the invention being set forth in the following claims.

What is claimed is:

1. A shoulder and arm stabilizing restraint device that is configured to isolate a shoulder joint of a user by supporting a respective forearm of the user, the device comprising:
   a pillow;
   a forearm support extending along a portion of said pillow;
   a forearm strap connected to said forearm support, said forearm strap configured to extend to and connect to said pillow such that said forearm support provides a shelf upon which the user's forearm may comfortably rest; and
   a hand strap traversing an anterior face of said pillow, said hand strap being configured to selectively restrain a hand of a user of the device when the device is in use,
   wherein said forearm support is permanently attached to said pillow such that the forearm support hangs loose from said pillow when said forearm strap is not connected to said pillow.

2. The device of claim 1, wherein said forearm support defines opposed medial and lateral faces, and wherein said forearm support is attached to said pillow at said medial face of said forearm support.

3. The device of claim 2, wherein said pillow defines opposed medial and lateral faces, wherein said medial face of said pillow is configured to next against a torso of the user, and wherein said forearm support is attached to said pillow at said lateral face of said pillow.

4. The device of claim 3, wherein said forearm support is covered in fabric, said pillow is covered in fabric, and the fabric of said forearm support at the medial face is sewn to the fabric of said pillow at the lateral face.

5. The device of claim 2, wherein said forearm strap engages with said lateral face of said forearm support when the device is in use.

6. The device of claim 1, further comprising a waist strap connected to said pillow.

7. The device of claim 1 further comprising a shoulder strap, said shoulder strap comprising a first end connected to an anterior point of said pillow, a second end connected to a posterior point of said pillow, and an intermediate scalloped portion configured to traverse a clavicle area.

8. The device of claim 1, wherein said forearm support is permanently attached to said pillow with glue or a zipper.

* * * * *